(12) United States Patent
Mack et al.

(10) Patent No.: US 10,002,635 B2
(45) Date of Patent: Jun. 19, 2018

(54) SYSTEMS AND METHODS FOR INFORMATION CAPTURE

(71) Applicant: SENWORTH, INC., Cameron Park, CA (US)

(72) Inventors: David Matthias Mack, Cameron Park, CA (US); Brian Dempsey Dold, Placerville, CA (US)

(73) Assignee: SENWORTH, INC., Cameron Park, CA (US)

( * ) Notice: Subject to any disclaimer, the term of this patent is extended or adjusted under 35 U.S.C. 154(b) by 0 days. days.

(21) Appl. No.: 15/345,249

(22) Filed: Nov. 7, 2016

(65) Prior Publication Data

US 2017/0133051 A1     May 11, 2017

Related U.S. Application Data

(60) Provisional application No. 62/253,596, filed on Nov. 10, 2015.

(51) Int. Cl.
| | | |
|---|---|---|
| *G11B 19/02* | (2006.01) | |
| *A41D 1/00* | (2018.01) | |

(Continued)

(52) U.S. Cl.
CPC ............. *G11B 19/02* (2013.01); *A41D 1/002* (2013.01); *A41D 19/0027* (2013.01);
(Continued)

(58) Field of Classification Search
CPC ...... A41D 1/002; A41D 19/0027; H04N 5/77; H04N 5/2252; H04N 1/212; H04N 7/185;
(Continued)

(56) References Cited

U.S. PATENT DOCUMENTS 5,096,287 A     3/1992  Kakinami et al.
9,298,575 B2 *  3/2016  Tamari .............. G06F 11/3013
(Continued)

FOREIGN PATENT DOCUMENTS

CA     2924688 A1    4/2015
EP     0985899 A1    3/2000

OTHER PUBLICATIONS

International Search Report and Written Opinion for PCT/US2016/060923 filed Nov. 8, 2016, dated Jan. 31, 2017.

*Primary Examiner* — Robert Chevalier
(74) *Attorney, Agent, or Firm* — R. Whitney Johnson; Stoel Rives LLP

(57) ABSTRACT

Disclosed herein are information capture systems and related methods. An information capture system includes a sensor secured to an object configured to be involved with a possible event. The sensor is configured to detect one or more stimuli that are associated with the possible event, and transmit a sensor signal indicating data corresponding to the one or more stimuli. The information capture system also includes a recording device configured to record information responsive to a triggering event determined from the sensor signal. A method includes analyzing sensor data from the sensor, determining, from the sensor data, that a triggering event occurred, and recording post-trigger information following the determination of the triggering event.

20 Claims, 5 Drawing Sheets

(51) Int. Cl.
*A41D 19/00* (2006.01)
*A42B 1/24* (2006.01)
*A42B 3/04* (2006.01)
*A43B 3/00* (2006.01)
*G11B 20/02* (2006.01)
*G11B 20/10* (2006.01)
*H04N 1/21* (2006.01)
*H04N 5/225* (2006.01)
*H04N 5/77* (2006.01)
*H04N 7/18* (2006.01)
*A61B 5/024* (2006.01)

(52) U.S. Cl.
CPC .............. *A42B 1/242* (2013.01); *A42B 3/042* (2013.01); *A43B 3/0005* (2013.01); *G11B 20/02* (2013.01); *G11B 20/10* (2013.01); *H04N 1/212* (2013.01); *H04N 5/2252* (2013.01); *H04N 5/77* (2013.01); *H04N 7/185* (2013.01); *A61B 5/02438* (2013.01); *G11B 2020/10851* (2013.01)

(58) Field of Classification Search
CPC ......... G11B 20/10; G11B 20/02; G11B 19/02; G11B 2020/10851; A43B 3/0005; A42B 3/042; A42B 1/242; A61B 5/02438
USPC ................ 386/228, 226, 227, 229, 248, 326
See application file for complete search history.

(56) References Cited

U.S. PATENT DOCUMENTS

| | | |
|---|---|---|
| 2002/0085843 A1 | 7/2002 | Mann |
| 2006/0082730 A1 | 4/2006 | Franks |
| 2008/0061991 A1 | 3/2008 | Urban et al. |
| 2014/0277833 A1 | 9/2014 | Palan |
| 2015/0198406 A1 | 7/2015 | Ling |

* cited by examiner

SYSTEMS AND METHODS FOR INFORMATION CAPTURE

RELATED APPLICATION

This application claims the benefit under 35 U.S.C. § 119(e) of U.S. Provisional Application No. 62/253,596, filed Nov. 10, 2015, the entire disclosure of which is hereby incorporated herein by this reference.

TECHNICAL FIELD

The disclosure relates generally to systems and methods for information capture, and more particularly to sensor-triggered image data capture.

DETAILED DESCRIPTION

Figure 1:
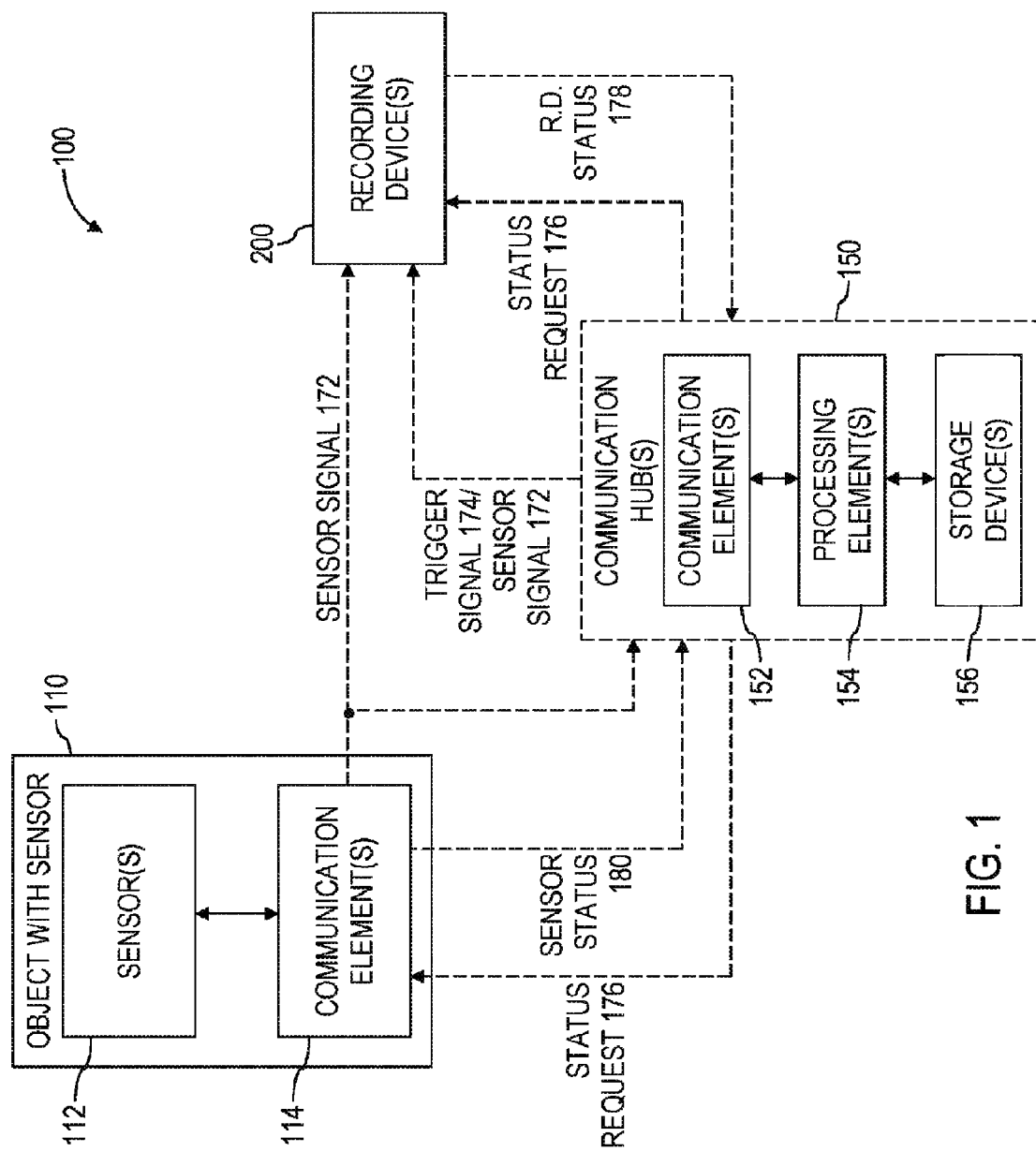
FIG. 1 is a simplified block diagram of an information capture system, according to one embodiment.

In the following detailed description, reference is made to the accompanying drawings, which form a part hereof, and in which is shown by way of illustration specific embodiments in which the present disclosure may be practiced. These embodiments are described in sufficient detail to enable those of ordinary skill in the art to practice the disclosure made herein. It should be understood, however, that the detailed description and the specific examples, while indicating examples of embodiments of the disclosure, are given by way of illustration only, and not by way of limitation. From the disclosure, various substitutions, modifications, additions, rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus or all operations of a particular method.

Information and signals described herein may be represented using any of a variety of different technologies and techniques. For example, data, instructions, commands, information, signals, bits, symbols, and chips that may be referenced throughout the description may be represented by voltages, currents, electromagnetic waves, magnetic fields or particles, optical fields or particles, or any combination thereof. Some drawings may illustrate signals as a single signal for clarity of presentation and description. It should be understood by a person of ordinary skill in the art that the signal may represent a bus of signals, wherein the bus may have a variety of bit widths and the present disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more computer-readable instructions (e.g., software code) on a computer-readable medium. Computer-readable media includes both computer storage media (i.e., non-transitory media) and communication media including any medium that facilitates transfer of a computer program from one place to another.

Elements described herein may include multiple instances of the same element. These elements may be generically indicated by a numerical designator (e.g., 200) and specifically indicated by the numerical indicator followed by an alphabetic designator (e.g., 200A). For ease of following the description, for the most part, element number indicators begin with the number of the drawing on which the elements are introduced or most fully discussed. Thus, for example, element identifiers on a FIG. 1 will be mostly in the numerical format 1xx, and elements on a FIG. 3 will be mostly in the numerical format 3xx.

As used herein, the term "object with sensor" refers to any object that includes a sensor that is capable of detecting events that occur in proximity to the object.

As used herein the term "recording device" refers to devices capable of recording information corresponding to events that occur in proximity to the object. For example, recording devices may include image capture devices capable of capturing images. As used herein, the term "image capture device" refers to digital and analog image capture devices, such as, for example, digital cameras, digital camcorders, analog cameras, analog camcorders, webcams, other image capture devices known in the art, and combinations thereof. As used herein, the term "image" refers to both still images and video images. As used herein, the term "still image" refers to an image having a single frame. Also, as used herein, the term "video image" refers to an image having multiple frames. Furthermore, as used herein, the terms "image data" and "video data" refer to data corresponding to one or more images that have been captured by an image capture device. "Image data" and "video data" include sufficient information for a rendering device, such as a computing device, to reconstruct for presenting the one or more images (e.g., either of a lossless and a lossy reconstruction) corresponding to the image data. "Image data" may be analog data or digital data. "Image data" and "video data" may refer to uncompressed image data or video data, or image data or video data that has been compressed (e.g., using any of a variety of image compression protocols). "Image data" may refer to both video image data and still image data. "Video image data" refers to data corresponding to a series of still images that are configured to be viewed consecutively.

As used herein, the term "in proximity to an object" refers to locations that are close enough to the object to trigger a sensor of the object. Often, events that are close enough to the object to trigger the sensor may also be close enough to a recording device to enable the recording device to record information corresponding to the event that triggers the sensor.

Embodiments of the disclosure include various information capture systems that are automatically triggered through sensor stimuli, and related methods.

FIG. 1 is a simplified block diagram of an information capture system 100. The information capture system 100 may include an object with sensor 110 including an object configured to be involved with a possible event (e.g., a future, upcoming, and/or anticipated event), and one or more sensors 112 (hereinafter "sensor" 112) secured to the object. The sensor 112 may be configured to detect one or more stimuli that are associated with the possible event and transmit a sensor signal 172 (e.g., using one or more communication elements 114 operably coupled to the sensor 112) indicating data corresponding to the one or more stimuli. The information capture system 100 may also include one or more recording devices 200 (hereinafter "recording device" 200) configured to record information (e.g., still images, video images, audio, heat readings, and combinations thereof) responsive to a triggering event determined from the data indicated by the sensor signal 172. In this way, the recording device 200 may record information about the possible event responsive to a determination that a triggering event has occurred.

In some embodiments, the object with sensor 110 may include sports equipment, and the recording device 200 may be configured to record information (e.g., video) responsive to activity involving the sports equipment. By way of non-limiting example, the object with sensor 110 may include a surfboard, a skateboard, a snowboard, a wakeboard, a ski, a bicycle, a motorcycle, a kayak, a stand-up paddle board, a canoe, an all-terrain vehicle (ATV), an automobile, a ramp, a ball, a baseball bat, a golf club, a hockey stick, a goal (e.g., a basketball rim, a hockey or soccer goal, etc.), and other sports equipment. As a specific, non-limiting example, the object with sensor 110 may include a surfboard, and the recording device 200 may be configured to record video responsive to a sensor 112 secured to the surfboard sensing that a user stood up on the surfboard. Of course, each type of sports equipment may have different detectable stimuli associated therewith that may correspond to events of interest for recording with the recording device 200.

In some embodiments, the object with sensor 110 may include a wearable device. By way of non-limiting example, the object with sensor 110 may include a gun holster, a heart-rate monitor, a glove, an article of clothing, a hat, a helmet, a watch, a bracelet, an armband, a leg band, a headband, a shoe, and other wearable devices. As a specific, non-limiting example, the object with sensor 110 may include a gun holster, and the recording device 200 may include a dash video camera in a law-enforcement vehicle or a body camera worn by a law-enforcement officer wearing the gun holster. The dash video camera may record video responsive to a law-enforcement officer drawing the gun from the holster. Similarly, the body camera may begin recording video responsive to the law enforcement officer drawing the gun from the holster. Of course, many different applications may correspond to each of the different wearable devices, and may be associated with a variety of different stimuli.

Other examples of the object with sensor 110 may include a walking stick, a mirror, a window, a door, and any other object that may receive stimuli corresponding to possible events of interest for recording corresponding information.

In some embodiments, the sensor 112 may include a biometric sensor. By way of non-limiting example, the sensor 112 may include an accelerometer, a heart-rate sensor, a body temperature sensor, a pedometer, other biometric sensors, and combinations thereof. In such embodiments, information corresponding to events that trigger biometric responses in a person may be recorded responsive to certain biometric triggers (e.g., a heart-rate above a predetermined level, an accelerative force above a predetermined threshold, accelerometer readings corresponding to a certain type of activity, etc.).

In some embodiments the sensor 112 may include other accelerometers (e.g., non-biometric), a pressure sensor, a capacitive touch sensor, a heat sensor, a temperature sensor, a gyroscope, a motion sensor, an infrared sensor, a light sensor, an acoustic sensor, a moisture sensor, a strain gauge, an image sensor, a proximity sensor, an ambient light sensor, a connector that senses when the connector is connected and disconnected, a global positioning system (GPS) sensor, other sensors, and combinations thereof. Accordingly, various types of stimuli may trigger the recording device 200 to record information. In some embodiments, multiple sensors 112 may be included.

In some embodiments, the sensor 112 may be configured to transmit the sensor signal 172 wirelessly. In such embodiments, the communication elements 114 may include at least a wireless communication device. By way of non-limiting example, the wireless communication device may be configured to communicate using Bluetooth, low power Bluetooth, WiFi, Zigbee, mobile wireless networks (e.g., long term evolution (LTE), 3G, etc.), other wireless communication protocol, or combinations thereof. In some embodiments, the communication elements 114 may be configured to enable the sensor 112 to communicate using a wired communication link (e.g., Universal Serial Bus (USB), Firewire (IEEE 1394), Ethernet (IEEE 802.3), other wired communication links, or combinations thereof). In some embodiments, the sensor 112 may be configured to transmit the sensor signal 172 securely. In some embodiments, the communication elements 114 include a global positioning system (GPS) device (which could be used to cause the recording device 200 to trigger responsive to the recording device 200 being positioned at a predetermined position, or within a predetermined range of the predetermined position).

In some embodiments, the recording device 200 may include an image capture device (e.g., secured to a dashboard of a vehicle, to a person, to a bicycle, etc.) configured to capture one or more images responsive to the triggering event. By way of non-limiting example, the image capture device may include a video image capture device 200A (FIG. 2) configured to record video responsive to the triggering event determined from the data indicated by the sensor signal 172. In some embodiments, the recording device 200 may include an audio recording device in addition to, or instead of, an image capture device. In some embodiments, the recording device 200 may include more than one recording device. In some embodiments including multiple recording devices 200, any one of the recording devices 200 that is triggered to start recording may transmit instructions (e.g., wirelessly, via wired communications, etc.) to others of the recording devices 200 to start recording. In some embodiments, the recording device 200 may be configured to start recording responsive to a user of the information capture system manually activating the recording device, in addition to recording responsive to triggering events detected by the sensor 112.

In some embodiments, the sensor 112 may include a geolocation sensor. By way of non-limiting example, the sensor 112 may be configured to trigger responsive to a user or object entering or leaving vicinity (e.g., a predetermined range) of the sensor 112. Also by way of non-limiting example, a communication element may be placed in a desired location designed to continuously or intermittently transmit a detect signal within a predetermined range to allow geolocated activation and/or threshold activation of the recording device 200 whenever it comes within the area of interest. The recording device 200 could be configured to stop recording when it has gone outside of the range of the geolocated transmitter, which covers the area of interest. As a specific, non-limiting example, a geolocated trigger may be placed at a ski jump and a camera starts recording when a skier comes close to the jump and stops recording when the skier leaves the jump. Also by way of non-limiting example, a GPS could be used such that a recording device 200 is triggered responsive to a person or object arriving or leaving a location (e.g., a specific global position or positions) or vicinity thereof. For example, the recording device 200 could be activated by its actual global position as determined by a GPS and a user predefined location.

In some embodiments, the recording device 200 (or recording devices 200) may be configured to stop recording responsive to a triggering event detected by the sensor 112, responsive to a manual user input, or combinations thereof. In some embodiments where there are multiple recording devices 200, any one of the recording devices 200 that is controlled to stop recording may also communicate (e.g., wirelessly, via wired communications, etc.) to the others of the multiple recording devices 200 indicating that the others of the multiple recording devices 200 should stop recording.

As a specific non-limiting example, the recording device 200 may include a video image capture device 200A (see, e.g., FIG. 2) configured to constantly record and store a recent segment of video data, even before detecting the triggering event. The video image capture device 200A may also be configured to delete portions of the video data that were recorded at least a predetermined buffer period of time before a present time (e.g., 1, 2, 5, 10 seconds, etc. before the present time). The video image capture device 200A may further be configured to stop deleting the video data that was recorded the predetermined buffer period of time before the present time responsive to the triggering event. In this way, the video image capture device 200A may be capable of recording video data corresponding to events leading up to the triggering event without accruing a relatively large amount of video data. One way that additional storage space may be freed up is to record video before the triggering event at a different (e.g., lower) resolution than video that is recorded after the triggering event. More detail regarding an example of a video image capture device 200A is discussed below with reference to FIG. 2.

As another specific, non-limiting example, the recording device 200 may be equipped with a low power communication element (e.g., a low power Bluetooth device) that stays continuously on. The low power communication element may be capable of receiving the sensor signal 172 and/or the trigger signal 174, and provide instructions to the recording device 200 to power on and begin recording. Accordingly, the sensor signal 172 and/or the trigger signal 174 may effectively wake up the recording device 200.

As a relatively more generalized non-limiting example, the recording device 200 may be configured to constantly record and store information, and delete the information that was recorded a predetermined buffer period of time before a present time. When a triggering event is detected from the data indicated in the sensor signal 172, the recording device 200 may be configured to stop deleting the information that was recorded the predetermined buffer period of time before the present time. In some embodiments, the recording device 200 may be configured to stop recording a predetermined amount of time after being triggered to stop recording.

In some embodiments, the recording device 200 may include a wearable recording device. By way of non-limiting examples, the recording device 200 may include a law-enforcement body camera, a helmet camera, a camera integrated into a pair of glasses, a camera integrated into a watch, other wearable recording devices, or combinations thereof.

In some embodiments, the information capture system 100 may include one or more communication hubs 150 (sometimes referred to herein simply herein as "hub" 150) in electrical communication with the sensor 112 and the recording device 200 (e.g., using one or more communication elements 152). The hub 150 may be configured to receive the sensor signal 172 from the sensor 112, and transmit a trigger signal 174 to the recording device responsive to detecting the triggering event from the sensor signal 172.

In some embodiments, the hub 150 may include a personal computing device (e.g., a smartphone, a tablet computer, a laptop computer, a desktop computer, a personal digital assistant (PDA), other personal computing device, or combinations thereof). In such embodiments, the hub 150 may be configured to communicate with at least one of the sensor 112 and the recording device 200 through a personal area network (PAN), a local area network (LAN), or a combination thereof with or without intervention from a wide area network (WAN) (e.g., the Internet). In some embodiments, the hub 150 may include one or more cloud server devices configured to engage in electrical communications with at least one of the sensor 112 and the recording device 200 through at least a WAN.

In some embodiments, the hub 150 may be configured to transmit status requests 160 to at least one of the sensor 112 and the recording device 120, and receive status information (e.g., sensor status 180, R.D. status 178, or a combination thereof) from the at least one of the sensor 112 and the recording device 120. By way of non-limiting example, the hub 150 may transmit a status request 160 requesting information indicating a battery level, health parameters, other information, and combinations thereof, to the at least one of the sensor 112 and the recording device 200. The hub 150 may, in response, receive at least one of the sensor status 180 and the R.D. status 178 from the sensor 112 and the recording device 200, respectively.

The hub 150 may include one or more processing elements 154 (e.g., a central processing unit (CPU), a microcontroller, a programmable logic controller (PLC), other processing elements, or combinations thereof) operably coupled to one or more storage devices 156 (hereinafter "storage" 156). The storage 156 may include volatile data storage (e.g., random access memory), non-volatile data storage (e.g., read-only memory, Flash memory, electrically programmable read-only memory (EPROM), compact discs (CDs), digital versatile discs (DVDs), etc.), other data storage devices, or combinations thereof. The storage 156 may be implemented with one or more semiconductor devices, optical storage media, magnetic tape, other data storage media, devices configured to read and/or write data to such data storage devices, and combinations thereof.

The storage 156 may include computer-readable instructions configured to instruct the processing elements 154 to perform operations that the hub 150 is configured to perform. By way of non-limiting example, the computer-readable instructions may be configured to instruct the processing elements 154 to analyze the data indicated by the sensor signal 172. The computer-readable instructions may also be configured to instruct the processing elements 154 to determine that a triggering event has occurred responsive to the sensor signal 172. Examples of triggering events may include sensor readings surpassing a predetermined threshold, demonstrating a recognizable pattern or output, other events, and combinations thereof.

In operation, the sensor 112 may detect information about events occurring in proximity to the object with sensor 110. The sensor 112 may transmit the sensor signal 172 including the information about the events to at least one of the recording device 200 and the hub 150 through the communication elements 114. The information from the sensor signal 172 may be processed by one of the recording device 200 and the hub 150 to determine if a triggering event occurred. If a triggering event occurred, the recording device 200 may record information corresponding to the events that occur in proximity to the object. The recording device 200 may stop recording the information a predetermined amount of time after the triggering event, in response to a manual input to the recording device 200, in response to another detected event, in response to a command received from one of the sensor 112 and the hub 150, or combinations thereof.

In this way, information (e.g., video data) may be recorded responsive to an event that is detectable by the sensor 112 without the need for a manual input or timer to start the recording. For example, a gun holster may include the sensor 112, and the recording device 200 may include a dashboard video recording device in a law-enforcement officer vehicle that records video responsive to the gun being drawn from the gun holster. Accordingly, potentially legally relevant video footage of events following (and even leading up to) the drawing of the gun from the gun holster may be captured by the dashboard video recording device without the need for the law enforcement officer to constantly accrue video footage or take the time to manually start the recording during a crisis or emergency.

In some embodiments, the sensor signal 172 may itself be a trigger signal such that the recording device 200 starts recording responsive to receiving the sensor signal 172 (e.g., directly from the sensor 112 or through the hub 150). In such embodiments, the sensor signal 172 may not need to be processed by the recording device 200 or the hub 150.

In some embodiments, the object with sensor 110 may also include processing circuitry, similar to the hub 150. In such embodiments, processing of the sensor signal 172 may occur at the object with sensor instead of, or in addition to, at the recording device 200 or the hub 150.

In some embodiments, the recording device 200 may also be configured to record information responsive to a manual input. Accordingly, a user may start recording even if no triggering event is detected automatically from data indicated by the sensor signal 172.

Figure 2:
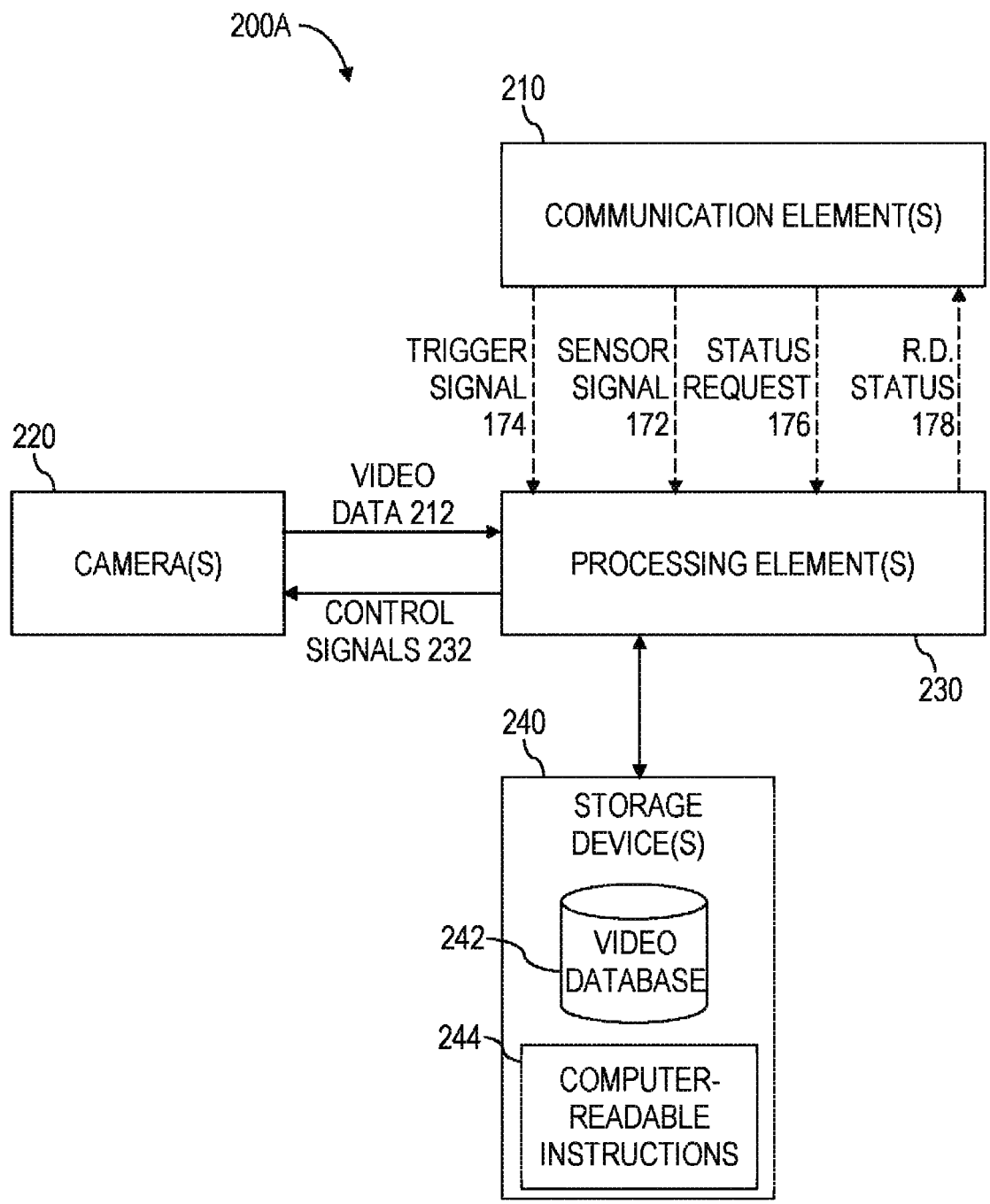
FIG. 2 is a simplified block diagram of an example of a recording device of the information capture system of FIG. 1.

FIG. 2 is a simplified block diagram of an example of a recording device 200A of the information capture system 100 of FIG. 1. The recording device 200A may include one or more processing elements 230 (hereinafter "processing elements" 230) operably coupled to one or more communication elements 210, one or more data storage devices 240 (hereinafter "storage" 240), and at least one camera 220 (e.g., a video camera). The processing elements 230 may include processing elements similar to those discussed above with reference to the processing elements 154 of the communication hub 150 of FIG. 1. The processing elements 230 may also include hardware elements (e.g., application specific integrated circuits, field-programmable gate arrays, etc.) configured to perform specialized functions related to image capture, image data storage, and sensor data analysis.

The storage 240 may include a video database 242 configured to store video data 212 captured by the camera 220. The storage 240 may also include computer-readable instructions 244 stored thereon. The computer-readable instructions 244 may be configured to instruct the processing elements to perform functions of the recording device 200A. By way of non-limiting example, the computer-readable instructions 244 may be configured to instruct the processing elements to control the camera 220 (e.g., activating, deactivating, focusing, adjusting a viewing angle, etc.) by transmitting control signals 232 to the camera. Also by way of non-limiting example, the computer-readable instructions 244 may be configured to instruct the processing elements to communicate with at least one of the sensors 112 (FIG. 1) and the hub 150 (FIG. 1) through the communication elements 210. By way of non-limiting example, the computer-readable instructions 244 may be configured to instruct the processing elements 230 to respond to status requests 176 from the hub 150.

The communication elements 210 may be similar to the communication elements 114 of the object with sensor 110 and/or the communication elements 152 the communication hub 150 of FIG. 1 (e.g., including wireless communication equipment, wired communication equipment, or combinations thereof). Accordingly, the recording device 200A may be configured to communicate with at least one of the object with sensor 110 (FIG. 1), and the hub 150 (FIG. 1) wirelessly, and/or through wired electrical connections. Specifically, the processing elements 230 may be configured to receive at least one of a sensor signal 172, a trigger signal 174, and the status request 176 through the communication elements 210. The processing elements 230 may also be configured to transmit recording device status signals 178 (sometimes referred to herein simply as "R.D. status" 178) through the communication elements 210.

In operation, the processing elements 230 may receive one of the trigger signal 174 and the sensor signal 172 through the communication elements 210. If the trigger signal 174 is received, the processing elements 230 may transmit control signals 232 to the camera 220 instructing the camera 220 to capture video data 212 (or stop deleting pre-trigger buffer video data stored in the video database 242 if buffer video is being captured). If the sensor signal 172 is received, the processing elements 230 may, in some embodiments, process the sensor signal 172 to determine if a triggering event occurred. If the triggering event occurred, the processing elements 230 may instruct the camera 220 to capture the video data 212 (or stop deleting the pre-trigger buffer video data). The processing elements 230 may store the video data 212 captured by the camera 220 in the video database 242 of the storage 240. The processing elements may continue storing video data 212 in the video database until a determination is made to stop recording (e.g., responsive to a sensor, expiration of a predetermined time from the triggering event, etc.).

In some embodiments, the processing elements 230 may be configured to provide (through the communication elements 210) a video stream (e.g., to an electronic display or other electronic device) of the video data 212 stored in the video database 242. The video stream may include a real-time video stream or delayed video stream. In some embodiments, the processing elements 230 may be configured to share the video data 212 (or compressed versions thereof) stored in the video database 242 with a cloud storage server (not shown) remote from the recording device 200A.

Figure 3:
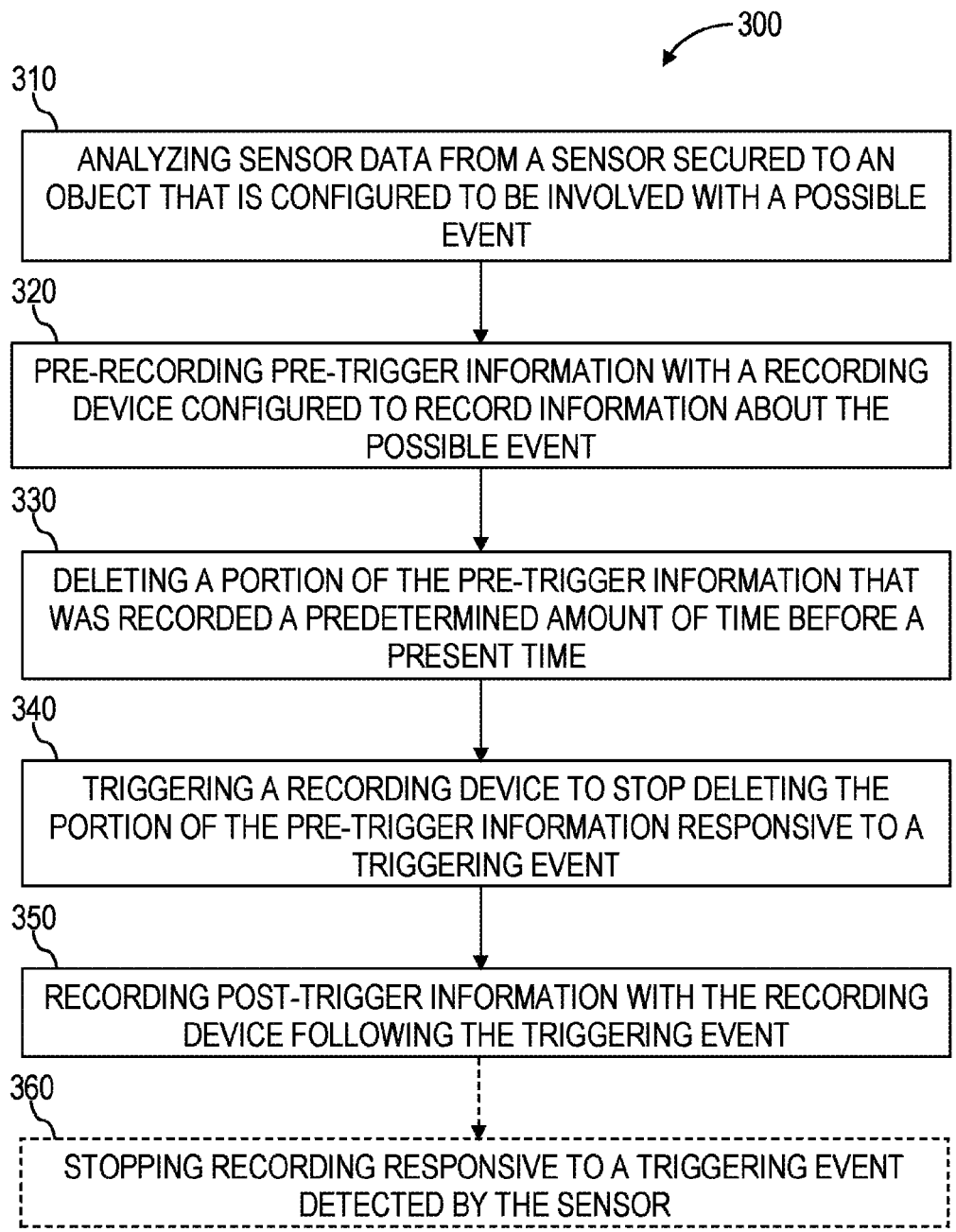
FIG. 3 is a simplified flowchart of an example method of information capture, according to one embodiment.

FIG. 3 is a simplified flowchart of an example method 300 of information capture, according to one embodiment. The method may be performed by an information capture system, such as the information capture system 100 of FIG. 1. At operation 310, the method 300 may include analyzing sensor data from a sensor 112 (FIG. 1) secured to an object 110 that is configured to be involved with a possible event. In some embodiments, analyzing sensor data may include determining if a triggering event occurred. In some embodiments, determining if a triggering event occurred may include comparing the sensor data to a predetermined threshold, to a predetermined pattern, and combinations thereof.

At operation 320, the method 300 may include pre-recording pre-trigger information with a recording device 200 (FIGS. 1 and 2) configured to record information about the possible event. In some embodiments, pre-recording pre-trigger information may include maintaining a predetermined amount of pre-trigger sensor information (e.g., video data) in a database (e.g., a video database). At operation 330, the method may include deleting a portion of the pre-trigger information that was recorded a predetermined amount of time before a present time.

At operation 340, the method 300 may include triggering the recording device 200 (FIGS. 1 and 2) to stop deleting the portion of the pre-trigger information responsive to determining, from the sensor data, that a triggering event occurred. In some embodiments, determining a triggering event occurred includes determining the triggering event occurred with at least one of the sensor 112 (FIG. 1), the recording device 200 (FIGS. 1 and 2), and the hub 150 (FIG. 1). In some embodiments, triggering a recording device to stop deleting the portion of the pre-trigger information includes transmitting one of a trigger signal 174 and a sensor signal 172 (FIG. 1) to the recording device 200.

At operation 350, the method 300 may include recording post-trigger information with the recording device 200 (FIGS. 1 and 2) following the determination that the triggering event occurred. In some embodiments, recording post-trigger information may include recording video data 212 with a different resolution than pre-trigger video data. In some embodiments, recording post-trigger information may include recording video data 212 with a higher resolution than pre-trigger video data.

At operation 360, in some embodiments, the method 300 may include stopping recording responsive to a triggering event detected by the sensor 112.

Figure 4A:
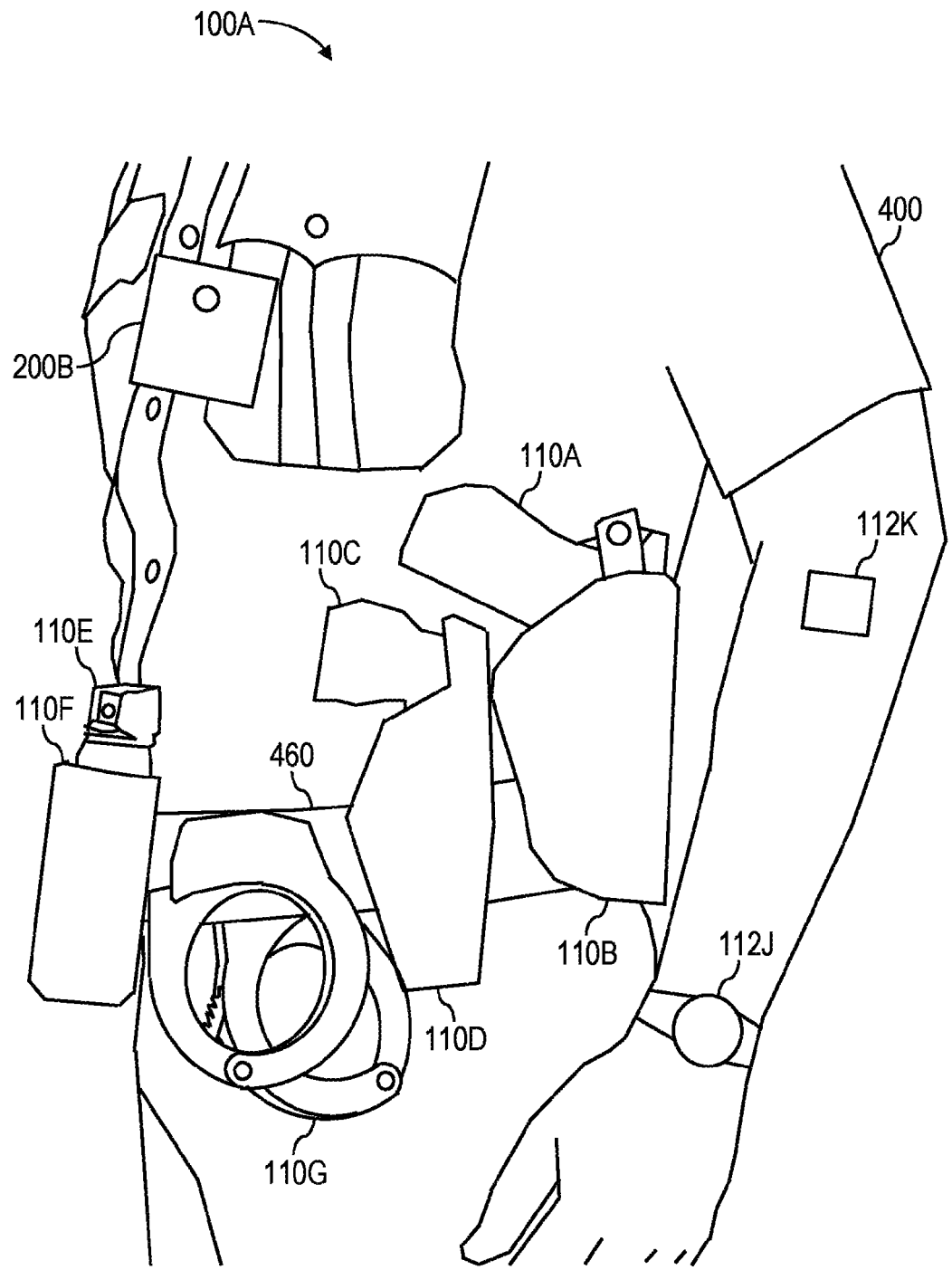
FIGS. 4A and 4B illustrate a specific, non-limiting example of an information capture system, according to one embodiment.
Figure 4B:
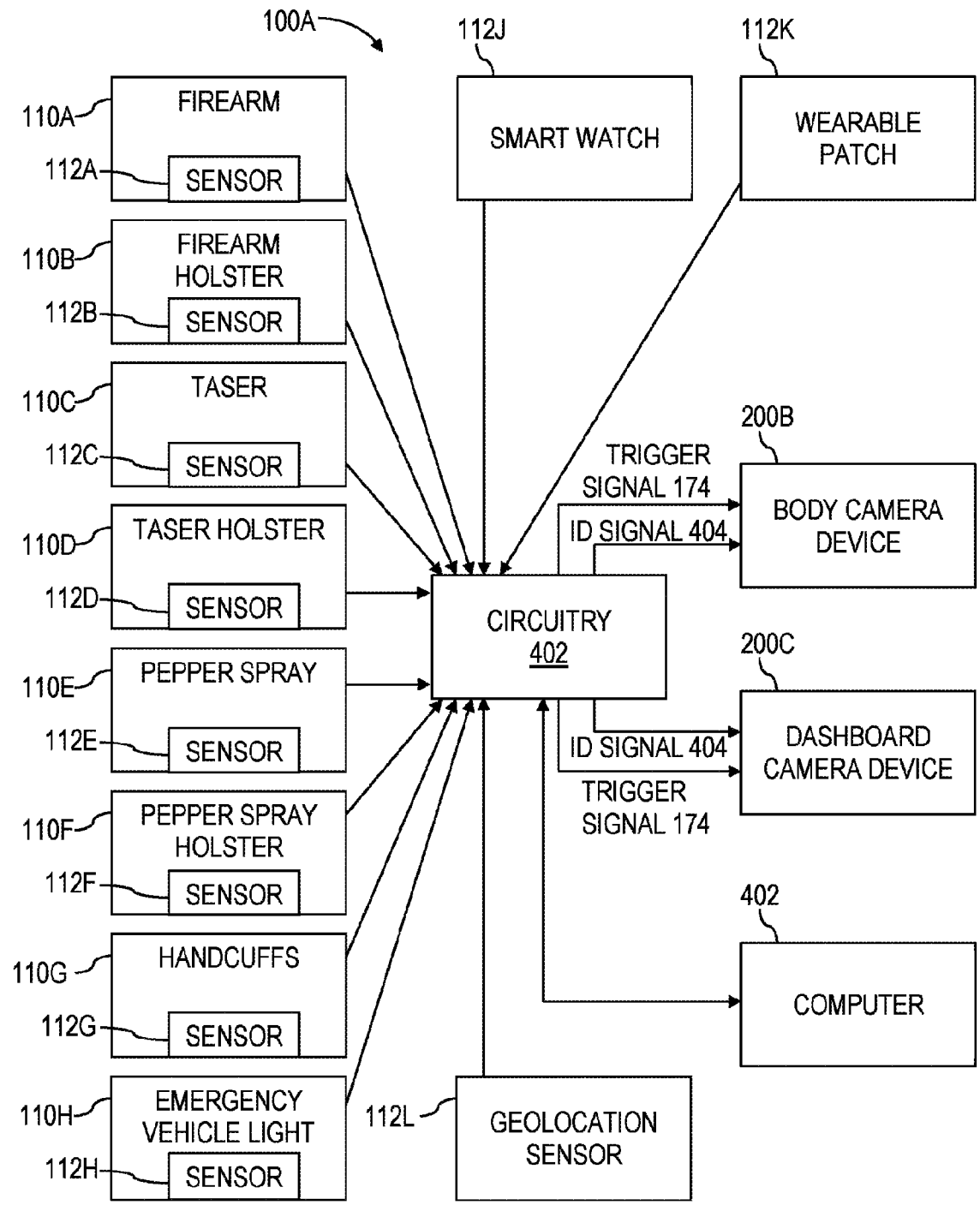

FIGS. 4A and 4B illustrate a specific, non-limiting example of an information capture system 100A, according to some embodiments.

FIG. 4A is a simplified view of a portion of the information capture system 100A on a law enforcement officer 400 (e.g., a police officer, a special agent, a military officer, etc.). The portion of the system 100A illustrated in FIG. 4A includes a body camera device 200B worn by the law enforcement officer 400, and various objects 110A, 110B, 110C, 110D, 110E, 110F, and 110G (a firearm 110A, a firearm holster 110B, a taser 110C, a taser holster 110D, a pepper spray can 110E, a pepper spray holster 110F, and handcuffs 110G) that may be used in association with actions of the law enforcement officer 400. FIG. 4A illustrates the firearm 110A, the firearm holster 110B, the taser 110C, the taser holster 110D, the pepper spray can 110E, the pepper spray holster 110F, and the handcuffs 110G secured to the law enforcement officer 400 by a belt 460. The portion of the system 100A of FIG. 4A also includes a smart watch 112J and a wearable patch 112K.

FIG. 4B is a simplified block diagram of the information capture system 100A. Although not illustrated in FIG. 4A, the information capture system 100A may include a dashboard camera device 200C instead of, or in addition to, the body camera device 200B. Other recording devices may also be included. The body camera device 200B, the dashboard camera device 200C, and any other camera device may be similar to the recording device 200A of FIG. 2. As also not illustrated in FIG. 4A, the information capture system 100A may include a computer 402 (e.g., for use in an emergency vehicle, using programs such as a Computer Aided Dispatch System, a Record Management Systems, etc.) and a geo-location sensor 112L. As further not illustrated in FIG. 4A, the information capture system 100A may include an emergency vehicle light 110H in addition to the objects 110A-G illustrated in FIG. 4A. The objects 110A-H may include sensors 112A-H, respectively, configured to detect potential actions of the law enforcement officer 400 involving the use of the objects 110A-110H.

By way of non-limiting example, the sensor 112A of the firearm 110A may be configured to detect when the law enforcement officer 400 is preparing to use the firearm 110A (e.g., the sensor 112A may be configured to detect a draw of the firearm 110A from the holster, a safety mechanism switching from an "on" position to an "off" position, and/or a firing of the firearm 110A). Also by way of non-limiting example, the sensor 112B of the firearm holster 110B may be configured to detect when the law enforcement officer 400 is preparing to use the firearm 110A (e.g., the sensor 112B may be configured to detect when the firearm 110A is withdrawn from the firearm holster 110B). As a specific, non-limiting example, the sensor 112B of the firearm holster 110B may include a mechanical button (a button that is normally open, normally closed, etc. that is undepressed when the firearm 110A is removed) or a flex sensor (i.e., a sensor that changes electrical properties such as resistance or capacitance responsive to a flex of the flex sensor) in the bottom of the firearm holster 110B that detects a withdrawal of the firearm 110A from the firearm holster 110B. As other specific, non-limiting examples, the sensor 112B may be attached to side of the holster 110B (e.g., an inside side of the holster 110B), near the top of the holster 110B, or anywhere within or without the holster 110B. In some embodiments, multiple sensors 112B (e.g., of the same type, of different types, etc.) may be used on or in the holster 110B to ensure that withdrawal of the firearm 110A is properly detected. As a further, non-limiting example, the sensor 112B or sensors 112B may be configured to detect movement of holster safety systems that prevent undesired drawing of the firearm, such as a self-locking system or thumb-break snaps.

It should be noted that many different types of holsters exist for many different types of firearms, and the configuration and positioning of the sensor 112B or sensors 112B may vary for different types of holsters. Accordingly, sensors compatible with holsters and firearms that are commonly used by law enforcement officers may be used. Alternatively, the holsters themselves may include sensors in some embodiments.

The sensor 112B or sensors 112B should be durable, and may be inexpensive enough to be disposable. They should be small, yet have a battery life that is relatively long (e.g., years at a time). If not built into the holster 110B, the sensor 112B should be easily applied to the holster 110B. One approach is to include the sensor 112B in a guard at the bottom of the holster 110B. A guard (e.g., a plastic guard) that comes with the holster 110B may be replaced with the guard including the sensor 112B. The guard may include a mechanical button for the sensor 112B that may be pressed by a structural element of the firearm 110A (e.g., by a light attached below a barrel, etc.). Mechanical locks that hold the firearm 110A in place within the holster 110B may prevent false triggers.

Another approach is to clip the sensor 112B to the top rim of the holster 110B on the outside of the holster 110B. The sensor 112B may include a flex sensor or a spring steel lever inside the holster 110B that runs a distance (e.g., a few inches) down the wall of the holster 110B from the top rim. Other approaches may involve using a hall effect sensor, a reed switch, a proximity sensor, a capacitive touch sensor, a pressure sensor, other sensors, or combinations thereof.

Combinations of sensors 112B may also be used on or in the holster 110B. For example, for looser holsters 110B (e.g., leather holsters), pressure sensors may be installed in multiple locations in the holster 110B in combination with a spring steel lever button at the top of the holster 110B. To avoid false positives, the cameras 200B, 200C may only be triggered if all of the pressure sensors detect no pressure and the spring steel lever button is decompressed. Accordingly, even if the firearm 110A moves around within the holster 110B, the cameras 200B, 200C will not trigger as long as one of the sensors 112B does not trigger.

As another example of a combination of sensors, a close range proximity sensor could be used in conjunction with a mechanical switch and/or flex sensor attached to the safety mechanism on the holster 110B that secures the firearm 110A. When the law enforcement officer 400 moves or unlatches the safety mechanism, the mechanical switch and/or flex sensor triggers the close range proximity sensor to power up. The proximity sensor may be used to ensure that the cameras 200B, 200C are activated only when the gun is drawn, but the proximity sensor may only be functioning after the law enforcement officer 400 removes the safety mechanisms on the holster 110B. As a result, errors may be prevented, and battery power for the proximity sensor may be conserved. To further conserve power, the frequency and length of time signals from the proximity sensor are transmitted may be adjusted, as long as enough of the activation signal is present to transmit the message. The transmit range of the proximity sensor can also be adjusted to turn on cameras of other nearby law enforcement officers to record sensitive situations from as many angles as possible.

Similar to the sensors 112A and 112B detecting possible uses of the firearm 110A by the law enforcement officer 400, the sensors 112C-112H may be configured to detect possible uses of the objects 110C-110H corresponding thereto.

The use of the objects 110A-110H by the law enforcement officer 400 may often accompany sensitive situations in which the law enforcement officer 400 may be, among other things, engaging in combat, exerting physical force, disabling a person, restraining a person, or signaling a motorist to pull over for a traffic stop. These sensitive situations sometimes escalate, resulting in unfortunate circumstances, and even human injury or death in some situations. Conduct of the law enforcement officer 400 or those the law enforcement officer 400 interacts with may sometimes later be investigated to determine whether some improper action was taken by either party. In order to aid in these investigations, the use of the objects 110A-110H may lead to a triggering of the body camera device 200B, the dashboard camera device 200C, or a combination thereof to record video images (e.g., including video images alone, or a combination of video images and audio). The recorded video images may later be studied during post-incident investigations.

The information capture system 100A includes circuitry 402 configured to trigger (e.g., to record, to stop recording, to stop deleting recordings taken a predetermined threshold period of time before being triggered, etc.) the body camera device 200B and the dashboard camera device 200C (and any other camera devices) responsive to detections by the sensors 112A-H that the law enforcement officer 400 may be about to use or stop using one of the objects 110A-110H. For example, the circuitry 402 may be configured to provide a trigger signal 174 to the body camera 200B and/or the dashboard camera device 200C. In some embodiments, the trigger signal 174 may be configured to trigger the body camera device 200B and the dashboard camera device 200C to start or stop recording video images. In embodiments where there are multiple different camera devices, the camera devices may be capable of communicating with each other (e.g., wirelessly, via wired communications, etc.), and triggering each other to start or stop recording even if only one of the camera devices is triggered (e.g., by a triggering event, manually, or a combination thereof). As a specific, non-limiting example, the dashboard camera device 200C may be triggered to automatically start recording (and/or keep stored video from a predetermined buffer period of time before the dashboard camera device 200C is triggered) when the firearm 110A is drawn from the holster 110B, and to automatically stop recording when the firearm 110A is replaced into the holster 110B. The dashboard camera device 200C may also transmit signals to the body camera device 200B to start and stop recording.

In some embodiments, the trigger signal 174 may be configured to trigger the body camera device 200B and the dashboard camera device 200C to stop deleting video images that were recorded outside of a predetermined buffer period of time before the trigger so that events leading up to the use of the object 110A-110H may be recorded. In other words, the body camera device 200B and the dashboard camera device 200C may be configured to continuously record and store only a most recent portion of the video images corresponding to a predetermined length of time while deleting video images not of the most recent portion before the circuitry triggers the video recording device. Then, responsive to the trigger signal 174, the body camera device 200B and the dashboard camera device 200C may be configured to stop deleting the video images not of the most recent portion of the video images. In some embodiments, about thirty seconds of video may be maintained in the video recording device at a time before the trigger signal 174, resulting in thirty seconds of video leading up to the detected use of the object 110A-110H.

The circuitry 402 may also be configured to provide an identification (ID) signal 404 to the body camera device 200B and the dashboard camera device 200C. The ID signal 404 identifies which of the sensors 112A-112L and/or which of the objects 110A-110H triggered the trigger signal 174. The body camera device 200B and the dashboard camera device 200C may be configured to store information (e.g., in the storage devices 240) indicating the sensors 112A-112L and/or objects 110A-110H that triggered the trigger signal 174. Accordingly, a record of not only events following and leading up to the triggering event, but also of what object or sensor triggered the triggering event, may be recorded by the body camera device 200B and the dashboard camera device 200C.

In some embodiments, the circuitry 402 includes wireless communication circuitry. By way of non-limiting example, the circuitry 402 may include low-power, local area network (LAN) wireless communication circuitry (e.g., low power Bluetooth) communicating with the communication elements 210 (e.g., low power wireless communication circuitry) of the body camera device 200B and the dashboard camera device 200C. Although some well-known local area network communications employ a pairing function between devices, low power Bluetooth may operate without pairing (which may consume less electrical power than operating with pairing). Also, low power Bluetooth enables unidirectional communications (e.g., communication from the circuitry 402 to the body camera device 200B and the dashboard camera device 200C). In some embodiments, the circuitry 402 may be configured to communicate using low power Bluetooth, without undergoing pairing functions and only engaging in unidirectional communications. In this way, power savings may enable the use of a low capacity battery (e.g., a button battery) without requiring battery replacement for months or years at a time.

In some embodiments, a pairing function may be employed between the circuitry 402 and the body camera device 200B and the dashboard camera device 200C (e.g., using conventional Bluetooth). In some embodiments, the circuitry 402 may employ other wireless communications (e.g., WiFi communications, cellular wireless networks, Zigbee networks, etc.). In some embodiments, the circuitry 402 may employ wired communications. By way of non-limiting example, the belt 460 may serve as a wire harness interfacing the sensors 112A-H, the circuitry 402, and the body camera device 200B. In some embodiments, the circuitry 402 may employ both wired and wireless communications.

In some embodiments, each object 110A-110H may include its own circuitry 402. In some embodiments, the circuitry 402 may be separate from the objects 110A-110H. In some embodiments, the circuitry 402 may be incorporated into the objects 110A-110H.

In some embodiments, the information capture system 100A may only include one or some of the objects 110A-110H and/or sensors 112A-112L. By way of non-limiting example, the system 100A may only include the firearm 110A, the firearm holster 110B, and the firearm holster sensor 112B. In some embodiments, the information capture system 100A may include other objects and sensors instead of or in addition to the objects 110A-110H and 112A-112H. By way of non-limiting example, the information capture system 100A may include body armor or a bullet-proof vest equipped with a sensor or sensors, which would enable triggering of the body camera device 200B and the dashboard camera device 200C responsive to a detected impact (e.g., a gunshot or other blow to the body of the law enforcement officer 400). Also by way of non-limiting example, a bumper of a law-enforcement vehicle may be equipped with a sensor to enable triggering of the body camera device 200B and the dashboard camera device 200C responsive to an impact (e.g., an impact with another vehicle or stationary object).

As a further non-limiting example, the geolocation sensor 112L may trigger the body camera device 200B when the law enforcement officer 400 enters a predetermined location (e.g., a prison cell, a crime scene, etc.). The geolocation sensor 112L may also trigger the body camera device 200B (e.g., to record, to start accumulating or stop deleting recorded data, to stop recording, to stop accumulating or start deleting recorded data, etc.) when the law enforcement officer 400 leaves a predetermined location. By way of non-limiting example, the trigger may be responsive to the law enforcement officer 400 entering or leaving a range of the geolocation sensor 112L, which may be secured to a wall, a ceiling, or other stationary or mobile object that is located in a location of interest. This could also be performed with a global positioning system (GPS) device (e.g., within the smart watch 112J, the wearable patch 112K, the computer 402, etc.). For example, a trigger may occur responsive to the law enforcement officer 400 entering or leaving a predetermined location or vicinity (e.g., a preset range) of the predetermined location.

In some embodiments, the geolocation sensor 112L may function in conjunction with a motion detector (not shown). For example, the geolocation sensor 112L may function in a low-power mode to conserve power when the motion detector does not detect motion in the proximity of the Other sensors are contemplated herein (e.g., a sensor that generates a trigger responsive to the law enforcement vehicle exceeding a predetermined speed, a sensor built into a baton, a sensor built into a knife or a knife sheathe, etc.). For example, the smart watch 112J and/or the wearable patch 112K may include biometric sensors (e.g., heartrate sensors, accelerometers, gyrometers, etc.). As a specific, non-limiting example, if a heartrate of the law enforcement officer 400 elevates above a predetermined level, it may be determined that the law enforcement officer 400 is facing a sensitive situation (e.g., a situation requiring physical strain or evoking an emotional response that elevates the law enforcement officer's 400 heartrate, etc.). Also by way of non-limiting example, an accelerometer or gyrometer may be capable of sensing motions of or impacts to the law enforcement officer 400 that are likely to be associated with the law enforcement officer 400 sustaining an injury. These and other biometrically sensed events may trigger the body camera device 200B and/or the dashboard camera device 200C.

In some embodiments, any one or more of the sensors 112A-H may be configured to conserve power, while achieving an optimal or desired performance. To conserve power and reach optimal performance, the range, length, and frequency of the activation signals from the sensors 112A-H may be customized. By increasing range of the activation signal, the sensor may be able to reach the recording devices of other officers in close proximity so that events of interest may be captured from multiple angles. By decreasing the range, greater power conservation can be achieved.

In some embodiments, the information capture system 100A may only include one of the body camera device 200B and the dashboard camera device 200C.

In some embodiments, the information capture system 100A may include other recording devices 200 instead of or in addition to the body camera device 200B and the dashboard camera device 200C. By way of non-limiting example, the information capture system may include a recording device (e.g., video recording device, audio recording device, etc.) built into a pair of glasses, a helmet, a hat, or other wearable object.

In some embodiments, sensors 112 and cameras 200 of more than one law enforcement officer 400 may interact with each other to provide multiple triggers and/or recordings of multiple camera angles.

While certain illustrative embodiments have been described in connection with the figures, those of ordinary skill in the art will recognize and appreciate that embodiments encompassed by the disclosure are not limited to those embodiments explicitly shown and described herein. Rather, many additions, deletions, and modifications to the embodiments described herein may be made without departing from the scope of embodiments encompassed by the disclosure, such as those hereinafter claimed, including legal equivalents. In addition, features from one disclosed embodiment may be combined with features of another disclosed embodiment while still being encompassed within the scope of embodiments encompassed by the disclosure, as contemplated by the inventors.

The invention claimed is:

1. An information capture system, comprising:
   a sensor secured to an object configured to be involved with a possible event, the sensor configured to detect one or more stimuli that are associated with the possible event, and transmit a sensor signal indicating data corresponding to the one or more stimuli;
   at least one other sensor secured to another object configured to be involved with another possible event, the at least one other sensor configured to detect one or more other stimuli that are associated with the another possible event, and transmit another sensor signal indicating data corresponding to the one or more other stimuli;
   a recording device configured to record information responsive to a triggering event determined from the sensor signal, the another sensor signal, and a combination of the sensor signal and the another sensor signal; and
   circuitry configured to indicate which of the sensors corresponding to the object or the another object detected the possible event or the another possible event that led to the triggering of the recording device to record the information.

2. The information capture system of claim 1, wherein the recording device comprises a low power wireless communication device that is configured to:
   receive the sensor signal from the sensor;
   remain active while the video recording device is in an inactive state; and
   instruct the video recording device to power up to an active state and record the information responsive to the triggering event.

3. The information capture system of claim 1, wherein the object comprises an object selected from the group consisting of a surfboard, a skateboard, a snowboard, a wakeboard, a ski, a heart-rate monitor, a bicycle, a motorcycle, a kayak, a stand-up paddle board, a canoe, an all-terrain vehicle, an automobile, a ramp, a ball, a baseball bat, a golf club, a hockey stick, a glove, an article of clothing, a hat, a helmet, a watch, a bracelet, an armband, a leg band, a headband, a shoe, glasses, a walking stick, a mirror, and a door.

4. The information capture system of claim 1, wherein the sensor comprises at least one sensor selected from the group consisting of an accelerometer, a pedometer, a pressure sensor, a capacitive touch sensor, a temperature sensor, a heat sensor, a gyroscope, a heart-rate sensor, a motion sensor, an infrared sensor, a light sensor, an acoustic sensor, a moisture sensor, a strain gauge, an image sensor, an ambient light sensor, a proximity sensor, a connector that senses when the connector is connected and disconnected, a flex sensor, and a global positioning system sensor.

5. The information capture system of claim 1, wherein the recording device comprises a video image capture device configured to:
   constantly record and store video data;
   delete the video data that was recorded at least a predetermined buffer period of time before a present time; and
   stop deleting the video data that was recorded the predetermined buffer period of time before the present time responsive to the triggering event.

6. The information capture system of claim 5, wherein the video data that was recorded during the buffer period of time is of a different image resolution than the video data that was recorded after the triggering event.

7. The information capture system of claim 1, further comprising a communication device placed in a location, the communication device configured to transmit a detect signal within a predetermined range of the location to enable triggering of the recording device responsive to one or more of a geolocation activation or a threshold activation.

8. The information capture system of claim 1, wherein the recording device is configured to stop recording responsive to being moved outside of a predetermined range of a geolocated transmitter covering an area of interest.

9. The information capture system of claim 1, wherein the recording device comprises a wearable recording device.

10. The information capture system of claim 1, wherein the sensor includes a global positioning system (GPS) sensor, and the recording device is configured to be triggered responsive to a detection of the GPS sensor determining that the recording device is at least one of entering or exiting a predetermined location.

11. An information capture system, comprising:
    a sensor configured to generate a detect signal responsive to detecting a potential use of a firearm by a law enforcement officer;
    at least one other sensor configured to generate at least one other detect signal responsive to detecting a potential use, by the law enforcement officer, of one or more devices selected from a pepper spray can, a pair of handcuffs, body armor, and a bullet-proof vest;
    a video recording device configured to record video images of the potential use of the firearm and store the video images in a data storage device of the video recording device; and
    circuitry configured to trigger the video recording device responsive to the detect signal;
    wherein:
      the circuitry is further configured to trigger the video recording device responsive to the at least one other detect signal; and
      the circuitry is further configured to indicate which of the sensors for the firearm, the pepper spray can, the handcuffs, the body armor, and the bullet-proof vest detected the potential use that led to the circuitry triggering the video recording device.

12. The information capture system of claim 11, wherein the sensor comprises a firearm holster sensor configured to detect withdrawal of the firearm from the firearm holster.

13. The information capture system of claim 11, wherein the sensor is configured to generate the detect signal responsive to a firing of the firearm.

14. The information capture system of claim 11, wherein the sensor comprises a firearm safety sensor configured to generate the detect signal responsive to a safety mechanism of the firearm switching to an off position.

15. The information capture system of claim 11, wherein the video recording device is configured to:
   store only a most recent portion of the video images corresponding to a predetermined length of time stored in the data storage device while deleting video images not of the most recent portion before the circuitry triggers the video recording device responsive to the detect signal; and
   stop deleting the video images not of the most recent portion responsive to the circuitry triggering the video recording device.

16. The information capture system of claim 15, wherein the predetermined length of time is about thirty (30) seconds.

17. The information capture system of claim 1, wherein the object configured to be involved with the possible event comprises a firearm, the possible event comprises a use of the firearm by a law enforcement officer, and the another possible event comprises a potential use, by the law enforcement officer, of one or more devices selected from a pepper spray can, a pair of handcuffs, body armor, and a bullet proof vest.

18. The information capture system of claim 17, wherein the sensor secured to an object comprises a firearm holster sensor configured to detect withdrawal of the firearm from the firearm holster.

19. The information capture system of claim 1, wherein the at least one other sensor secured to another object comprises at least two other sensors secured to at least another two objects, respectively.

20. The information capture system of claim 1, wherein the sensor comprises a mechanical sensor configured for placement within a firearm holster, the mechanical sensor configured to displace and transmit the signal indicating the data corresponding to the one or more stimuli responsive to a firearm being withdrawn from the holster.

* * * * *